(12) United States Patent
Yoo et al.

(10) Patent No.: US 12,303,542 B2
(45) Date of Patent: May 20, 2025

(54) FUNCTIONAL FOOD COMPOSITION FOR ALLEVIATION OF IRRITABLE BOWEL SYNDROME

(71) Applicant: GREEN CROSS WELLBEING CORPORATION, Seoul (KR)

(72) Inventors: Young Hyo Yoo, Seoul (KR); Hae Jung Han, Seoul (KR); Jong Bok Yun, Seoul (KR); Joo Young Kim, Seoul (KR); Man Heun Kim, Seoul (KR)

(73) Assignee: GREEN CROSS WELLBEING CORPORATION, Seoul (KR)

( * ) Notice: Subject to any disclaimer, the term of this patent is extended or adjusted under 35 U.S.C. 154(b) by 0 days.

(21) Appl. No.: 17/637,332

(22) PCT Filed: Aug. 8, 2020

(86) PCT No.: PCT/KR2020/011154
§ 371 (c)(1),
(2) Date: Feb. 22, 2022

(87) PCT Pub. No.: WO2021/034139
PCT Pub. Date: Feb. 25, 2021

(65) Prior Publication Data
US 2022/0296665 A1 Sep. 22, 2022

(30) Foreign Application Priority Data

Aug. 22, 2019 (KR) .......................... 10-2019-0103194

(51) Int. Cl.
| | |
|---|---|
| *A61K 36/355* | (2006.01) |
| *A23L 33/105* | (2016.01) |
| *A61P 1/10* | (2006.01) |
| *A61P 1/12* | (2006.01) |
| *A61K 9/20* | (2006.01) |

(52) U.S. Cl.
CPC .......... *A61K 36/355* (2013.01); *A23L 33/105* (2016.08); *A61P 1/10* (2018.01); *A61P 1/12* (2018.01); *A61K 9/20* (2013.01); *A61K 2236/331* (2013.01); *A61K 2236/35* (2013.01)

(58) Field of Classification Search
None
See application file for complete search history.

(56) References Cited

U.S. PATENT DOCUMENTS

| | | | |
|---|---|---|---|
| 2012/0021011 A1* | 1/2012 | Kim | A61P 37/06 424/769 |
| 2013/0310454 A1 | 11/2013 | Yoo et al. | |
| 2015/0044316 A1* | 2/2015 | Yoon | A61P 29/00 424/778 |

FOREIGN PATENT DOCUMENTS

| | | |
|---|---|---|
| KR | 10-0878436 B1 | 1/2009 |
| KR | 10-2011-0055266 A | 5/2011 |
| KR | 10-1074839 B1 | 10/2011 |
| KR | 10-2012-0113879 A | 10/2012 |
| KR | 10-1605312 B1 | 3/2016 |
| KR | 10-1781121 B1 | 9/2017 |
| KR | 10-1964054 B1 | 4/2019 |

OTHER PUBLICATIONS

English translation of KR 101605312 (2016).*
English translation of KR 10-178121 B1 (2017).*
Xia (CN 105395915 A—English translation)—2016.*
Zhu (Am J Gastroenterol (2013), vol. 108, pp. 1516-1525).*
Yonghoon Choi et al., "The Efficacy and Safety of GCWB104 (Flos Lonicera Extract) in Functional Dyspepsia: A Single-Center, Randomized, Double-Blind, Placebo-Controlled Study", Gut and Liver, Jan. 2020, pp. 67-78, vol. 14, No. 1, (12 pages).
Anne Ferguson et al., "Frequency of "functional", gastrointestinal disorders", The Lancet, Sep. 17, 1977, pp. 613-614, 2(8038).
Francis Creed et al., "Psychological factors in the irritable bowel syndrome", Gut. 28, pp. 1307-1318 (1987).
A P Manning et al., "Toward positive diagnosis of irritable bowel", British Medical Journal. Sep. 2, 1978, pp. 653-654.
Michael Camilleri et al., "What's in a Name? Roll on Rome II", Gastroenterology, Feb. 1, 1998, vol. 114, Issue 2, P237, 4 pages.
Cengiz Pata et al., "Serotonin Transporter Gene Polymorphism In Irritable Bowel Syndrome", The American Journal of Gastroenterology, 2002, vol. 97, No. 7, pp. 1780-1784.
S M Collins, et al., "The putative role of inflammation in the irritable bowel syndrome", Gut, 2001, 49, pp. 743-745.
Sarah Moretti, et al., "Oxidative stress as a biomarker for monitoring treated celiac disease", Clinical and Translational Gastroenterology, 2018, pp. 157-167, 9.
Renata D'incà et al., "Oxidative DNA Damage in The Mucosa of Ulcerative Colitis Increases with Disease Duration and Dysplasia", Inflammatory bowel disease, Jan. 2004, pp. 23-27, vol. 10, No. 1.
Yujie Li, et al., "Lonicerae Japonicae Flos and Lonicerae Flos: A Systematic Pharmacology Review", Evidence-Based Complementary and Alternative Medicine, 2015, pp. 1-16, vol. 2015.
Eun Ju Lee et al., "Phytochemical studies on Lonicerae Flos (1)—Isolation of Iridoid Glycosides and other Constituents", Natural Product Sciences, 2010, pp. 32-38, vol. 16, No. 1.
Byoung Wook Bang et al., "BST-104, a Water Extract of Lonicera japonica, Has a Gastroprotective Effect via Antioxidant and Anti-Inflammatory Activities", Journal of medicinal food, 2019, pp. 1-12.
Cha Ho Yeol et al., "The Anti-oxidative and Anti-inflammatory Effect of Lonicera Japonica on Ulcerative Colitis Induced by Dextran Sulfate Sodium in Mice", J Pediatr Korean Med., Aug. 2015, pp. 54-64, 29(3).

(Continued)

*Primary Examiner* — Susan Hoffman
(74) *Attorney, Agent, or Firm* — Sughrue Mion, PLLC

(57) ABSTRACT

A functional food composition contains a *Lonicera japonica* extract as an active ingredient is disclosed. The functional food composition is useful in alleviating irritable bowel syndrome. The *Lonicera japonica* extract reduces diarrhea and/or intestinal intonation symptoms, thereby exhibiting an effect of alleviating irritable bowel syndrome. A method of treating or alleviating irritable bowel syndrome includes a step of administering a composition to a subject, wherein the composition contains a *Lonicera japonica* extract.

3 Claims, 3 Drawing Sheets

(56) References Cited

OTHER PUBLICATIONS

Juha Kauppi et al., "Increased Oxidative Stress in the Proximal Stomach of Patients with Barrett's Esophagus and Adenocarcinoma of the Esophagus and Esophagogastric Junction", Translational Oncology, Aug. 2016, pp. 336-339, vol. 9, No. 6.
Albayrak F et al., "Should increased levels of urinary 8-hydroxydeoxyguanosine in chronic gastritis imply intestinal metaplasia or gastric atrophy?", Southern Medical Journal, Aug. 1, 2010, 753-757, 103(8), 2 pages.
Jo Min-Seong, "Irritable Bowel Syndrome, which causes the lower abdomen to ache even with a little care", URL: http://www.ilyoseoul.co.kr/news/articleView.html?idxno=39123, 10 pages, Jun. 17, 2009.
Written Opinion for PCT/KR2020/011154, dated Feb. 25, 2021.
International Search Report for PCT/KR2020/011154, dated Feb. 25, 2021.
Shang et al., "*Lonicera japonica*Thunb.: Ethnopharmacology, phytochemistry and pharmacology of an important traditional Chinese medicine", Journal of Ethnopharmacology 138 (2011) pp. 1-21.
Cho et al., "*Epimedium koreanum* Nakai Water Extract Exhibits Antiviral Activity against Porcine Epidermic Diarrhea Virus In Vitro and In Vivo", Hindawi Publishing Corporation, Evidence-Based Complementary and Alternative Medicine, 2012, Article ID 985151, 10 pages, doi:10.1155/2012/985151.
Database WPI, Clarivate Analytics, Thomas Scientific, 2017, XP002809625.
Eun-Ha Kim et al., "Immunomodulaton and attenuation of lethal influenza A virus infection by oral administration with KIOM-C," Antiviral Research, 2013, vol. 98, pp. 386-393 (8 pages total), XP028546479.
Extended European Search Report issued Jul. 20, 2023 in EP Application No. 20855257.0.

\* cited by examiner

[Figure 1]
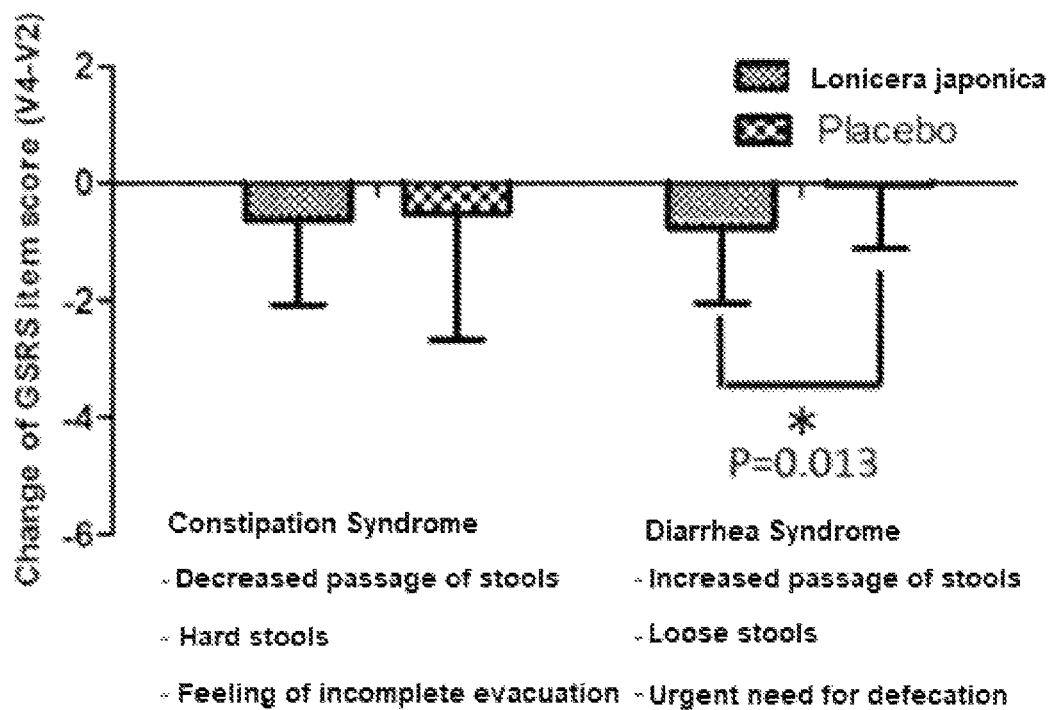

【Figure 2】
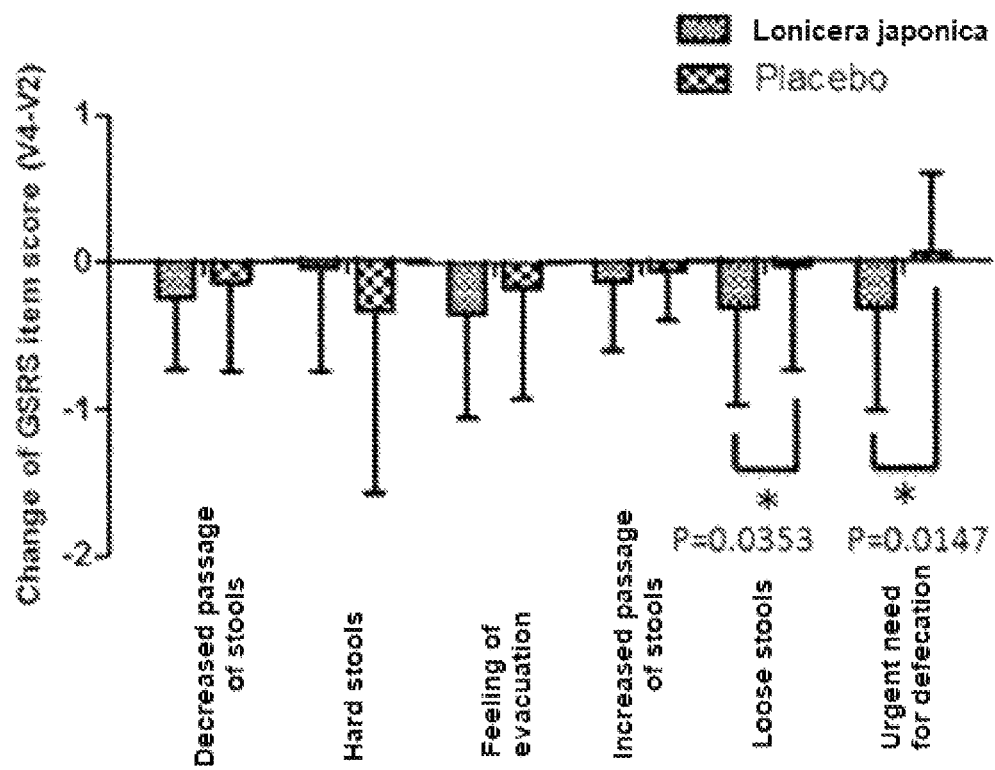
【Figure 3】
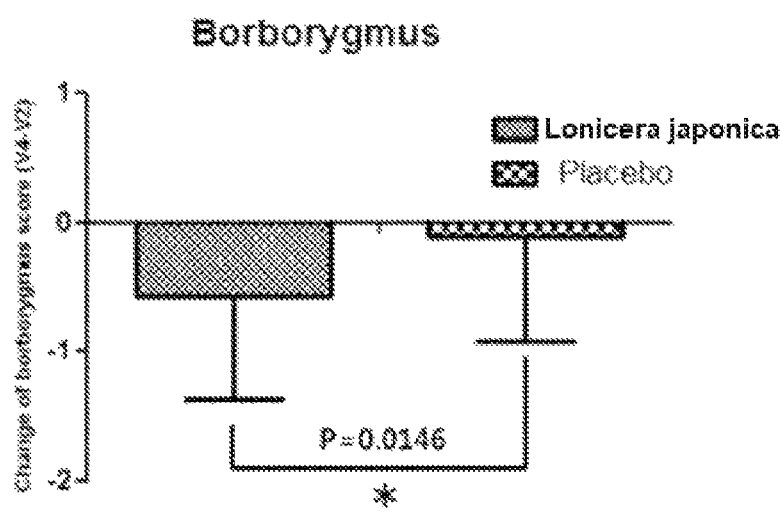

【Figure 4】
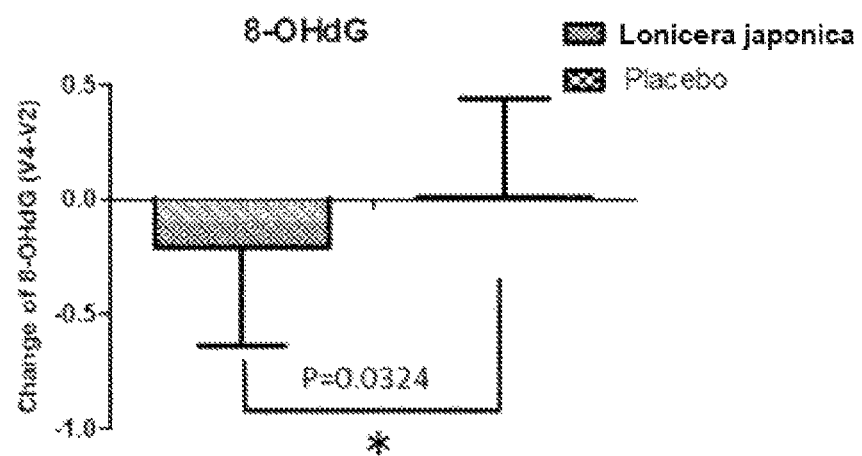

FUNCTIONAL FOOD COMPOSITION FOR ALLEVIATION OF IRRITABLE BOWEL SYNDROME

CROSS REFERENCE TO RELATED APPLICATIONS

This application is a National Stage of International Application No. PCT/KR2020/011154 filed Aug. 21, 2020, claiming priority based on Korean Patent Application No. 10-2019-0103194 filed Aug. 22, 2019, the entire contents of which are incorporated herein as part of the present specification.

TECHNICAL FIELD

The present invention relates to a functional food composition for alleviating irritable bowel syndrome, comprising a *Lonicera japonica* extract as an active ingredient.

BACKGROUND ART

Irritable bowel syndrome (IBS) is a chronic functional disorder characterized by lower abdominal bloating or discomfort, abdominal pain, frequent passage of stools, diarrhea or constipation or their alternating phenomenon, flatus, unpleasant odor, and the like, and is a clinical symptom characterized by non-specificity and diversity and the absence of anatomical or organic lesion abnormalities.

Irritable bowel syndrome is defined somewhat differently depending on the researcher, and according to Rome criteria II, which reflects recent research results on functional gastrointestinal diseases, it has been defined as a group including several functional bowel diseases in which abdominal discomfort or pain is associated with defecation or which are accompanied by changes in bowel habits or abnormal defecation features. According to the data reported by Manning et al. in 1978, four symptoms were statistically significantly common in patients with irritable bowel syndrome: abdominal pain improved by stools, loose stools when symptoms occurred, increased frequency of passage of stools when pain occurred, and abdominal bloating; and the two symptoms of mucous stool and feeling of incomplete evacuation also tended to be found more frequently in patients with irritable bowel syndrome.

For the diagnosis of irritable bowel syndrome symptoms, experts from various countries gathered in 1989 and presented the diagnostic criteria of Rome criteria I for various functional gastrointestinal diseases, and the irritable bowel syndrome was diagnosed when abdominal pain or abdominal discomfort accompanied by changes in the frequency of passage of stools or the shape of stools persists for more than 3 months, and two or more of the five defecation disorders such as (1) change in the frequency of passage of stools, (2) change in stool form, (3) abnormal stool evacuation, (4) mucous stool and (5) abdominal bloating are accompanied. These diagnostic criteria have been revised and complemented over the years, and Rome criteria II in 1999 and Rome criteria III in 2006 were revised. Currently, the most widely used criteria is Roman criteria II, and in the diagnostic method, irritable bowel syndrome was diagnosed when symptoms start at least 6 months before and the abdominal pain or abdominal discomfort due to defecation is alleviated for at least 3 days every month for the past 3 months, or when there is a change in frequency and shape. It is also classified into diarrhea type, constipation type, and alternating diarrhea and constipation type, which are the subtypes of irritable bowel syndrome.

Although the cause of irritable bowel syndrome is not clearly known, it is generally expected to occur due to complex causes such as changes in intestinal motility, visceral hypersensitivity, psychosocial factors, neurotransmitter imbalance, bacterial infection and inflammation. In addition, although the exact mechanism of irritable bowel syndrome has not been elucidated, according to recently reported data, a correlation with the concentration of serotonin among neurotransmitters has been revealed, and in particular, it is known that the concentration of serotonin in the blood is mainly influenced by the concentration of serotonin in the intestinal tract, which affects the diarrhea-dominant type of irritable bowel syndrome. Other mechanisms include a study on visceral stimulation derived from the gastrointestinal wall, a mechanism according to the interaction changed due to low-grade inflammation between mucosal immune system and afferent nerve endings distributed in the intestine, oxidative stress, and the like.

In particular, it has been reported that oxidative stress that causes DNA damage increases the ulceration of the intestinal mucosa, and in this case, 8-hydroxy-2'-deoxyguanosine (8-OHdG) is used as a mainly used biomarker. It has been reported that intestinal mucosa damage affects the diarrhea-predominant type symptom of irritable bowel syndrome.

Since the main cause of such irritable bowel syndrome is weak intestine or stress, the fundamental effect cannot be achieved by simply treating symptoms such as constipation and diarrhea, but it is expected that the fundamental effect will be achieved only by relieving stress. In addition, in order to develop a food or therapeutic agent capable of obtaining such an effect, studies to obtain an active ingredient from a natural product with no or fewer side effects are being actively conducted, but no significant results have been reported yet.

Recently, as research results of a *Lonicera japonica* extract among natural products on anti-inflammatory, antibacterial, antipyretic, hepatoprotective, anticancer, immune, anti-allergic, lipid metabolism, anti-arthritis and sedative effects have been published, interest in food or pharmaceutical uses of a *Lonicera japonica* extract is growing.

*Lonicera japonica* refers to dried flower buds or freshly blooming flowers of *Lonicera japonica* Thunberg belonging to the family Caprifoliaceae. Since ancient times, all parts such as stems, leaves, roots and flowers of *Lonicera japonica* have been used as medicinal herbs. In particular, it is recorded in the Chinese Pharmacopoeia as one of the drugs that has been used in traditional Chinese medicine (TCM) for thousands of years, and it is known in China that it has superior efficacy than *ginseng*. The flowers of *Lonicera japonica* are very fragrant and contain a lot of honey, and have a mild and slightly bitter taste. *Lonicera japonica* has been traditionally used for headaches, acute fever, sore throat, infectious diseases and the like, and through recent studies, various research results such as anti-inflammatory, antibacterial, antipyretic, hepatoprotective, anticancer, immune, anti-allergic, lipid metabolism, anti-arthritis and sedative effects have been reported.

Korean Patent No. 10-1605312 relates to a food composition for the treatment or prevention of gastrointestinal motility disorder using *Lonicera japonica* extract. Specifically, it discloses that the acetate fraction of the *Lonicera japonica* water extract is effective in improving the symptoms of gastrointestinal motility disorder, which is one or more of functional dyspepsia, constipation, irritable bowel symptoms, diabetic gastrointestinal motility disorder, gastrointestinal motility disorder caused by chemotherapy, intestinal atresia caused by gastrointestinal motility disorder, and gastrointestinal motility disorder caused by myotonic dystrophy. The above patent suggests the use of a *Lonicera japonica* extract for improving gastrointestinal motility disorders, but there is a problem that only mentions symptoms related to gastrointestinal motility and does not provide a solution for improving various symptoms occurring in the gastrointestinal tract.

As such, studies on food or drugs for improving symptoms of various gastrointestinal disorders in relation to a *Lonicera japonica* extract are continuing, but no specific research has been done on food or drugs related to the improvement of irritable bowel syndrome with diarrhea.

PRIOR ART REFERENCE (Patent Document 1) Korean Patent No. 10-1605312

DISCLOSURE

Technical Problem

Accordingly, it is an object of the present invention to provide a functional food composition for alleviating irritable bowel syndrome, comprising a *Lonicera japonica* extract as an active ingredient.

It is another object of the present invention to provide a pharmaceutical composition for preventing or treating irritable bowel syndrome, comprising a *Lonicera japonica* extract as an active ingredient.

Technical Solution

In order to achieve the above objects, the present invention provides a functional food composition for alleviating irritable bowel syndrome, comprising a *Lonicera japonica* extract as an active ingredient.

The present invention also provides a pharmaceutical composition for alleviating irritable bowel syndrome, comprising a *Lonicera japonica* extract as an active ingredient.

Advantageous Effects

According to the present invention, the *Lonicera japonica* extract exhibits an effect of alleviating the symptoms of irritable bowel syndrome by improving the symptoms of diarrhea. Specifically, the *Lonicera japonica* extract may alleviate irritable bowel syndrome by exhibiting an effect of improving increased passage of stools, loose stools, and urgent need for defecation.

In addition, the *Lonicera japonica* extract according to the present invention exhibits an effect of alleviating irritable bowel syndrome by improving the borborygmus, which is one of the symptoms related to irritable bowel syndrome.

In addition, the *Lonicera japonica* extract exhibits an effect of alleviating irritable bowel syndrome by reducing the blood concentration of 8-hydroxy-2'-deoxyguanosine (8-OHdG), which is used as a biomarker for oxidative stress.

In addition, among the *Lonicera japonica* extracts, a *Lonicera japonica* water extract may be more effective in alleviating borborygmus and/or irritable bowel syndrome with diarrhea.

DESCRIPTION OF DRAWINGS

FIG. 1 is a graph showing the results of evaluating the degree of improvement in constipation and diarrhea symptoms for the test group administered with the *Lonicera japonica* extract of Example 1 and the control group.

FIG. 2 is a graph showing the results of evaluating the degree of improvement of detailed symptoms related to constipation and diarrhea for the test group administered with the *Lonicera japonica* extract of Example 1 and the control group.

FIG. 3 is a graph showing the results of evaluating the degree of improvement in borborygmus symptoms for the test group administered with the *Lonicera japonica* extract of Example 1 and the control group.

FIG. 4 is a graph showing the results of hematological analysis related to the blood concentration of 8-OHdG for the test group administered with the *Lonicera japonica* extract of Example 1 and the control group.

BEST MODE

Hereinafter, the present invention will be described in more detail.

Food Composition

The present invention relates to a functional food composition for alleviating irritable bowel syndrome, comprising a *Lonicera japonica* extract as an active ingredient.

*Lonicera japonica* is a flower of *Lonicera japonica* Thunberg belonging to the family Caprifoliaceae, and is also called honeysuckle or *Lonicera japonica* Thunberg flower.

The *Lonicera japonica* extract may be extracted with a solvent selected from water, an alcohol having 1 to 4 carbon atoms, or a mixed solvent thereof.

The *Lonicera japonica* extract may be an organic solvent fraction of the *Lonicera japonica* extract. In this case, the organic solvent fraction of the *Lonicera japonica* extract refers to a substance obtained by independently or sequentially performing systematic fractionation of the *Lonicera japonica* extract using one or more of the following organic solvents.

The organic solvent may include one or more selected from the group consisting of hexane, ethyl acetate, dichloromethane, chloroform, and butanol.

For example, in consideration of the efficacy of alleviating irritable bowel syndrome, the organic solvent fraction of the *Lonicera japonica* extract may be an ethyl acetate fraction of the *Lonicera japonica* water extract as described below.

In addition, the *Lonicera japonica* extract may be a *Lonicera japonica* water extract extracted using water. The *Lonicera japonica* extract may be effective in alleviating symptoms of irritable bowel syndrome with diarrhea (disease code: K58.0) among irritable bowel syndrome.

According to the Gastrointestinal Symptom Rating Scale (GSRS), the diarrhea symptoms may include increased passage of stools, loose stools, and urgent need for defecation.

Therefore, the *Lonicera japonica* extract may alleviate symptoms of irritable bowel syndrome with diarrhea by improving the symptoms of increased passage of stools, loose stools and urgent need for defecation, which are symptoms of diarrhea.

In addition, the *Lonicera japonica* extract may improve borborygmus, which is a symptom related to irritable bowel disease. Borborygmus is a sound that occurs in the stomach and intestines, and when the amount of food is small and there is a lot of gas, or when the food is not digested and excessive gas is formed, a rumbling sound is generated in the process of liquid and gas advance due to the contraction of the stomach muscle, and the *Lonicera japonica* extract may alleviate the irritable bowel syndrome by improving the borborygmus.

The content of the *Lonicera japonica* extract is not particularly limited, but may be 0.1 to 10% by weight based on the total weight of the food composition, in consideration of the effect of alleviating symptoms related to irritable bowel syndrome as described above.

In the present invention, the formulations of the food composition are not particularly limited, but may be formulations such as a tablet, a capsule, a powder, a liquid, a granule, a pill, a piece, a paste, a syrup, a gel, a jelly, a caramel, a gummi, and a bar.

The food composition of the present invention may further include commonly used excipients and/or additives. The additive may be a binder, a disintegrant, a sweetener, a perfuming agent, a colorant, or a preservative, but is not limited thereto, as long as it is an additive commonly accepted in a food composition.

The excipient is not particularly limited in the present invention as long as the excipient is a substance added to facilitate ingestion of the preparation or to make a certain form. Examples of such excipients may include, but are not limited to, maltodextrin, starch, calcium carbonate, sucrose, lactose, glucose, mannitol, isomalt, xylitol, gelatin, (micro) crystalline cellulose, sorbitol, maltitol, hypromellose (HPMC), sodium lauryl sulfate, sodium alginate, calcium phosphate, and the like.

The binder is a substance that allows the shape of the preparation to be maintained, and may be, for example, one or more selected from water, an aqueous suspension of methacrylic acid copolymer, an aqueous ethyl cellulose suspension, an aqueous polyvinyl acetate suspension, and magnesium stearate.

The disintegrant is for promoting disintegration in the digestive tract in the body, and may be, for example, one or more selected from hydroxypropyl methylcellulose, bentonite, hydroxypropyl starch, sodium carboxymethylcellulose, sodium alginate, sodium lauryl sulfate, silicic anhydride, 1-hydroxypropylcellulose, dextran, starch, polyvinyl acetate, formaldehyde-treated casein and gelatin, alginic acid, amylose, guar gum, sodium bicarbonate polyvinylpyrrolidone, gum arabic, amylopectin, pectin, sodium polyphosphate, ethyl cellulose, sucrose, and magnesium aluminum silicate.

The sweetener serves to mask the bitter taste, and for example, white sugar, glucose, D-sorbitol, aspartame, licorice extract, erythritol, steviol glycosides, enzyme-treated stevioside and the like may be used.

As the perfuming agent, for example, orange oil, fruit juice extract, cinnamon oil, spearmint oil, peppermint water, vanilla, peppermint oil, rose oil, lemon oil, berry flavor, strawberry flavor, grape flavor, berry flavor, yogurt flavor and the like may be used.

As the colorant, for example, an artificial colorant such as a food synthetic colorant, a natural colorant such as a *gardenia* yellow colorant, a cochineal extract colorant, a caramel colorant, a Monascus colorant, and a saffron colorant and the like may be used.

As the preservative, for example, dehydroacetic acids, sorbic acids, benzoic acids, propionic acids, paraoxybenzoic acid esters and the like may be used.

In addition, the food composition of the present invention may further include additives such as commonly used a stabilizer, a thickener, an extender, or a pH adjuster.

In addition, there is no particular limitation on the type of the food. Examples of foods to which the *Lonicera japonica* extract may be added include meat, sausage, bread, chocolate, candy, snacks, pizza, ramen, other noodles, dairy products including ice cream, various soups, beverages, drinks, alcoholic beverages, vitamins mixtures and the like, and may include all health foods in a conventional sense.

The *Lonicera japonica* extract according to the present invention may be prepared by grinding *Lonicera japonica*, then adding an extraction solvent and heating them.

The extraction may be carried out at a temperature of 50 to 100° C., preferably 60 to 95° C. for 1 to 10 hours, preferably 3 to 7 hours.

After obtaining the *Lonicera japonica* extract, concentration of the extract may be further carried out, and the concentration may be performed at a temperature of 30 to 70° C. for 1 to 10 hours.

In addition, an excipient may be added for powdering of the concentrated *Lonicera japonica* extract, and examples of the excipient include maltodextrin, starch, lactose, crystalline cellulose and the like, and the powder may be prepared by mixing the *Lonicera japonica* extract and the excipient in a ratio of 10:90 to 50:50. After mixing with the excipient, the drying process of the extract may be carried out by vacuum drying, spray drying, or freeze drying, and through this process, a *Lonicera japonica* extract is prepared. The drying process may be performed at a temperature of 20 to 100° C. for 15 to 18 hours.

In this case, the extraction solvent may be selected from water, alcohol having 1 to 4 carbon atoms, and a mixed solvent thereof, and considering the efficacy of alleviating the symptoms of irritable bowel syndrome, the extraction solvent may be water.

In addition, by suspending the concentrated *Lonicera japonica* extract in water and then fractionating it with an organic solvent, an organic solvent fraction of the *Lonicera japonica* extract may be obtained.

Pharmaceutical Composition

The present invention relates to a pharmaceutical composition for alleviating irritable bowel syndrome, comprising a *Lonicera japonica* extract as an active ingredient, and the pharmaceutical composition may be a pharmaceutical composition for preventing or treating irritable bowel syndrome.

The irritable bowel syndrome is borborygmus and/or irritable bowel syndrome with diarrhea, and the irritable bowel syndrome with diarrhea may include one or more symptoms selected from the group consisting of increased passage of stools, loose stools, and urgent need for defecation.

In the present invention, the pharmaceutical composition may further include an excipient and/or an additive, and the excipient and/or additive are not particularly limited as long as they are pharmaceutically acceptable.

For example, the excipient may be maltodextrin, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, or mineral oil.

The additives may be a carrier, a diluent, a filler, an extender, a binder, a wetting agent, a disintegrant or a surfactant, commonly used in formulating a pharmaceutical composition.

In the present invention, the pharmaceutical composition comprising the *Lonicera japonica* extract as an active ingredient may be formulated into an oral or parenteral dosage form.

The formulation for oral administration may be, for example, one or more selected from the group consisting of a tablet, a pill, a hard/soft capsule, a solution, a suspension, an emulsion, a syrup and a granule.

In addition, the formulation for parenteral administration may be one or more selected from the group consisting of a sterile aqueous solution, a non-aqueous solution, a suspension, an emulsion, a freeze-dried preparation, and a suppository. The formulation for parenteral administration may be prepared in the form of a solution by mixing the *Lonicera japonica* extract in water with a stabilizer or buffer, and may be commercialized in a unit dosage form of ampoules or vials and injected by a subcutaneous injection, an intravenous injection, an intramuscular injection, or an intrathoracic injection.

The dosage of the pharmaceutical composition for alleviating irritable bowel syndrome comprising the *Lonicera japonica* extract of the present invention as an active ingredient is according to the doctor's prescription depending on factors such as the weight and age of the patient, and the specific nature and severity of the disease. However, as the oral or parenteral dosage required for adult treatment, it may be orally administered within the range of 100 to 2000 mg, preferably 100 to 1000 mg, more preferably 100 to 400 mg once or twice a day.

BEST MODE

Hereinafter, preferred examples will be provided to help understanding the present invention, but the following examples are only for illustrating the present invention. It will be apparent to those skilled in the art that various changes and modifications may be made within the scope and technical spirit of the present invention, and it is obvious that such changes and modifications fall within the scope of the appended claims.

Example 1: Preparation of *Lonicera japonica* Extract 100 g of flower buds of *Lonicera japonica* were dried and ground, and then extracted by putting them in 100 mL of purified water and heating them at 60° C. for 4 hours, and filtered, and concentrated at 30° C. for 2 hours to prepare an *Lonicera japonica* extract.

Thereafter, it was mixed with maltodextrin as an excipient for powdering the extract, and then dried under reduced pressure at a temperature of 40° C. for 14 hours to prepare 60 g of a *Lonicera japonica* extract in powder form.

Experimental Example 1: Gastrointestinal Symptom Rating Scale (GSRS) Evaluation

An experiment was conducted on the preventive or therapeutic efficacy for the symptoms of irritable bowel syndrome using the *Lonicera japonica* extract prepared in Example 1.

Specific test subjects, test methods, test items and test results are as follows:

1-1. Test Subject

Adult male and female over the age of 19

Subjects who are patients with upper abdominal discomfort or persistent/recurrent pain and patients diagnosed with functional dyspepsia (Rome criteria III) and do not require prompt drug treatment Subjects who can agree and sign written informed consent for human application test and cooperate with visits necessary for the research process, related tests and questionnaires and the like Participants: 92 people in total (test group: 46 people, control group: 46 people)

Final data analysis: 73 people in total (test group: 38 people, control group: 35 people)

1-2. Experimental Method

The *Lonicera japonica* extract prepared in Example 1 above was used as a tablet and used. The *Lonicera japonica* extract was prepared as a tablet of the *Lonicera japonica* extract (300 mg/1 tablet) by a conventional method. In this case, the content of the *Lonicera japonica* extract contained in the tablets was set to 125 mg/1 tablet.

For the test group, the *Lonicera japonica* extract tablets were administered twice a day, 1 tablet at a time for 8 weeks, and the administration dose of the *Lonicera japonica* extract was 250 mg/day.

For the control group, the tablets (300 mg/1 tablet) containing only the above maltodextrin were administered twice a day, 1 tablet at a time for 8 weeks.

1-3. Experiment Result (1) Evaluation Items

For the test group and control group that completed the experiment, a questionnaire related to the Gastrointestinal Symptom Rating Scale (GSRS) was conducted.

Table 1 below classifies the gastrointestinal and functional symptom scales.

TABLE 1

| Gastrointestinal Symptom Rating Scale (GSRS) | Abdominal pain | Abdominal pain |
|---|---|---|
| | | Sensation of stomach emptiness |
| | | Nausia and vomiting |
| | Reflux syndrome | Heartburn |
| | | Reflux syndrome |
| | Indigestion syndrome | Borborygmus |
| | | Abdominal distension |
| | | Eructation |
| | | Increased flatus |
| | Constipation syndrome | Decreased passage of stools |
| | | Hard stools |
| | | Feeling of incomplete evacuation |
| | Diarrhea syndrome | Increased passage of stools |
| | | Loose stools |
| | | urgent need for defecation |

Among the Gastrointestinal Symptom Rating Scale in Table 1 above, a questionnaire was conducted on 7 items including 3 items related to constipation symptoms, 3 items related to diarrhea syndrome and item related to irritable bowel disease-related borborygmus. The 7 items include borborygmus, which is a sound from the stomach; decreased passage of stools, hard stools, and feeling of incomplete evacuation, which are constipation symptoms; and increased passage of stools, loose stools, and urgent need for defecation symptoms, which are diarrhea symptoms.

(1) Evaluation Method

The degree of improvement for the symptoms specified in 7 items including the constipation symptoms, diarrhea symptoms and borborygmus symptom were classified into 4 grades, and then the degree of improvement for each item was evaluated for the test group and the control group, and the results were analyzed by the statistical analysis method, the Mann-Whitney U test, and the statistical analysis method before and after ingestion of the *Lonicera japonica* extract was tested using the Wilcoxon signed-rank test.

(2) Evaluation Results

FIG. 1 is a graph showing the results of evaluating the degree of improvement in constipation and diarrhea symptoms for the test group administered with the *Lonicera japonica* extract of Example 1 and the control group. Referring to FIG. 1, it can be seen that the test group administered with a *Lonicera japonica* extract of Example 1 (*Lonicera japonica* extract tablets) was significantly improved diarrhea symptoms compared to the control group (placebo). In the figure, the test group is denoted as "*Lonicera japonica*" and the control group is denoted as "placebo."

FIG. 2 is a graph showing the results of evaluating the degree of improvement of detailed symptoms related to constipation and diarrhea for the test group administered with the *Lonicera japonica* extract of Example 1 and the control group.

FIG. 3 is a graph showing the results of evaluating the degree of improvement in borborygmus symptoms for the test group administered with the *Lonicera japonica* extract of Example 1 and the control group.

In this case, detailed symptoms related to the above constipation and diarrhea include decreased passage of stools, hard stools, and feeling of incomplete evacuation, which are constipation symptoms; and increased passage of stools, loose stools, and urgent need for defecation symptoms, which are diarrhea symptoms.

Referring to FIG. 2, it can be seen that the test group administered with a *Lonicera japonica* extract of Example 1 (*Lonicera japonica* extract tablets) was significantly improved loose stools and urgent need for defecation symptoms, which are diarrhea symptoms, compared to the control group (placebo).

Referring to FIG. 3, it can be seen that the test group administered with a *Lonicera japonica* extract of Example 1 (*Lonicera japonica* extract tablets) was significantly improved borborygmus symptom compared to the control group (placebo).

In addition, Table 2 below shows the evaluation results for detailed symptoms related to constipation and diarrhea symptoms at the time points of before administration (baseline, Day 0), 4 weeks (Day 28) after administration and 8 weeks (Day 56) after administration of the *Lonicera japonica* extract tablets, for the test group and the control group.

TABLE 2

|  | Treatment | Baseline (0 day) | 28 day (4 weeks) | 56 day (8 weeks) |
|---|---|---|---|---|
| Decreased passage of stools | Placebo | 1.34 ± 0.59 | 1.20 ± 0.47 | 1.20 ± 0.58 |
|  | *Lonicera japonica* extract tablet | 1.39 ± 0.64 | 1.21 ± 0.47* | 1.16 ± 0.37** |
| Hard stools | Placebo | 1.71 ± 1.05 | 1.43 ± 0.70 | 1.37 ± 0.81 |
|  | *Lonicera japonica* extract tablet | 1.34 ± 0.67 | 1.50 ± 0.86 | 1.29 ± 0.52 |
| Feeling of incomplete evacuation | Placebo | 1.69 ± 0.72 | 1.51 ± 0.61 | 1.51 ± 0.61 |
|  | *Lonicera japonica* extract tablet | 1.71 ± 0.61 | 1.66 ± 0.67 | 1.37 ± 0.49** |
| Increased passage of stools | Placebo | 1.11 ± 0.32 | 1.09 ± 0.28 | 1.06 ± 0.24 |
|  | *Lonicera japonica* extract tablet | 1.24 ± 0.43 | 1.24 ± 1.47 | 1.11 ± 0.31 |
| Loose stools | Placebo | 1.23 ± 0.55 | 1.31 ± 0.47 | 1.20 ± 0.41 |
|  | *Lonicera japonica* extract tablet | 1.58 ± 0.60 | 1.47 ± 0.51 | 1.26 ± 0.45*,+ |
| Urgent need for defecation | Placebo | 1.17 ± 0.38 | 1.20 ± 0.41 | 1.23 ± 0.49 |
|  | *Lonicera japonica* extract tablet | 1.45 ± 0.65 | 1.29 ± 0.52 | 1.13 ± 0.41*,+ |
| Borborygmus | Placebo | 1.46 ± 0.70 | 1.31 ± 0.53 | 1.34 ± 0.54 |
|  | *Lonicera japonica* extract tablet | 1.66 ± 0.78 | 1.29 ± 0.46** | 1.08 ± 0.27****,+ |

(X ± SD) X= Mean, SD= Standard deviation;
*$p < 0.05$,
**$p < 0.01$,
***$p < 0.001$,
****$p < 0.0001$
Comparisons with baseline (Wilcoxon test for matched samples);
+$p < 0.05$,
++$p < 0.01$ Comparisons with placebo (Mann Whitney U test).

Referring to Table 2 above, it can be seen that the test group administered with the *Lonicera japonica* extract of Example significantly improved loose stools and urgent need for defecation symptoms, which are diarrhea symptoms, and borborygmus symptom, compared to the control group.

In addition, referring to Table 2 above, it can be seen that the test group administered with the *Lonicera japonica* extract of Example 1 significantly improved 5 out of 7 items, i.e., decreased passage of stools, feeling of incomplete evacuation, loose stools, urgent need for defecation symptoms and borborygmus, compared to before ingestion of the *Lonicera japonica* extracts. No significant improvement was found in the control group.

From these results, it can be seen that the *Lonicera japonica* extract according to the present invention is effective in improving irritable bowel syndrome, and in particular, diarrhea symptoms including loose stools, urgent need for defecation, and/or borborygmus symptoms are significantly improved, and thus, the *Lonicera japonica* extract is effective in improving irritable bowel syndrome with diarrhea.

Experimental Example 2

8-OHdG is a biomarker for measuring oxidative stress and is used as a biomarker indicative of DNA damage in cells, and thus, it has been reported to be associated with inflammatory diseases, especially irritable bowel syndrome, which is a disease related to the gastrointestinal tract (Kauppi J, Rasanen J, Sihvo E, Nieminen U, et al., Transl Oncol. 2016; 9:336-339; Albayrak F, Uyanik M H, Dursun H, Albayrak Y, et al., South Med J. 2010; 103:753-757). That is, as the blood concentration of 8-OHdG decreases, the symptoms of irritable bowel syndrome are improved.

Accordingly, for the test group of Experimental Example 1 and control group, hematological analysis was performed on the blood concentration of 8-OHdG, and the statistical analysis method, the Mann-Whitney U test was used.

FIG. 4 is a graph showing the results of hematological analysis related to the blood concentration of 8-OHdG for the test group administered with the *Lonicera japonica* extract of Example 1 and the control group.

Referring to FIG. 4, it can be seen that the test group administered with a *Lonicera japonica* extract of Example 1 (*Lonicera japonica* extract tablets) was significantly reduced the blood concentration of 8-OHdG compared to the control group (placebo).

Accordingly, it can be seen that the *Lonicera japonica* extract is effective in alleviating irritable bowel syndrome.

Although the present invention has been described above with reference to limited examples and drawings, the present invention is not limited thereto, and it will be apparent that various modifications and variations may be made within the scope of the technical spirit of the present invention and equivalents of the claims to be described below by those skilled in the art to which the present invention pertains.

The invention claimed is:

1. A method of alleviating a symptom of irritable bowel syndrome in a subject in need thereof, said method comprising administering a composition comprising a *Lonicera japonica* extract as an active ingredient to the subject,
   wherein the symptom of irritable bowel syndrome is borborygmus,
   wherein the *Lonicera japonica* extract is prepared by extracting the *Lonicera japonica* at a temperature of 50 to 100° C. for 3 to 7 hours to give an extract and then concentrating the extract at a temperature of 30 to 70° C. for 1 to 10 hours,
   wherein the *Lonicera japonica* extract is in a form of powder, and the *Lonicera japonica* extract powder is prepared by adding an excipient comprising maltodextrin, starch, lactose, crystalline cellulose, or a combination thereof to the extract to provide a mixture and then performing a drying of the mixture, said drying being selected from the group consisting of vacuum drying, spray drying, freeze drying, and a combination thereof, and said drying being carried out at a temperature of 20 to 100° C. for 15 to 18 hours, and
   wherein the alleviation of the symptom is an improvement of borborygmus severity degree, wherein the borborygmus severity degree reduces from 1.66±0.78 before intake of the composition (day 0) to 1.08±0.27 after daily intake for 56 days (day 56).

2. The method of claim 1, wherein the extracting is carried out with a solvent selected from water, an alcohol having 1 to 4 carbon atoms, or a mixed solvent thereof.

3. The method of claim 1, wherein the *Lonicera japonica* extract is included in an amount of 0.1 to 10% by weight based on the total weight of the composition.

* * * * *